United States Patent [19]

Darougar

[11] Patent Number: 5,137,030
[45] Date of Patent: Aug. 11, 1992

[54] DIAGNOSTIC METHODS

[75] Inventor: Sohrab Darougar, Croydon, England

[73] Assignee: Animal House, Inc., Portland, Me.

[21] Appl. No.: 415,646

[22] Filed: Oct. 2, 1989

Related U.S. Application Data

[63] Continuation-in-part of Ser. No. 913,944, Oct. 1, 1986, abandoned.

[51] Int. Cl.$^5$ .............................................. A61B 10/00
[52] U.S. Cl. .................................................... 128/757
[58] Field of Search ................................... 128/749–759

[56] References Cited

U.S. PATENT DOCUMENTS

| | | | |
|---|---|---|---|
| 3,540,432 | 11/1970 | Ayre | 128/758 |
| 3,724,463 | 4/1973 | Vail | 604/1 |
| 3,838,681 | 10/1974 | Dalton | 128/757 |
| 3,877,464 | 4/1975 | Vermes | 128/759 |
| 4,027,658 | 6/1977 | Marshall | 128/757 |
| 4,448,205 | 5/1984 | Stenkvist | 128/757 X |
| 4,757,826 | 7/1988 | Abdulhay | 128/757 |

FOREIGN PATENT DOCUMENTS 1173267 12/1969 United Kingdom ................ 128/757

*Primary Examiner*—Francis Jaworski
*Attorney, Agent, or Firm*—Paul J. Cook

[57] ABSTRACT

A probe is provided for collecting mucous tissue samples in vivo particularly from the conjunctiva, the urethra and the cervix. The probe comprises a handle portion and a body portion, which is slotted for scraping tissue into the slots.

The tissue sample may then be introduced into an aqueous transport medium comprising sucrose, potassium phosphates, foetal bovine serum, streptomycin, vancomycin and nystatin. The sample may be smeared from the transport medium, with the cells still intact onto a slide, using a cytocentrifuge; and then the smear is assayed for disease, for example disease due to adenovirus, herpes simplex virus or chlamydia.

The assay step may include single or multiple immunofluorescent staining.

21 Claims, 1 Drawing Sheet

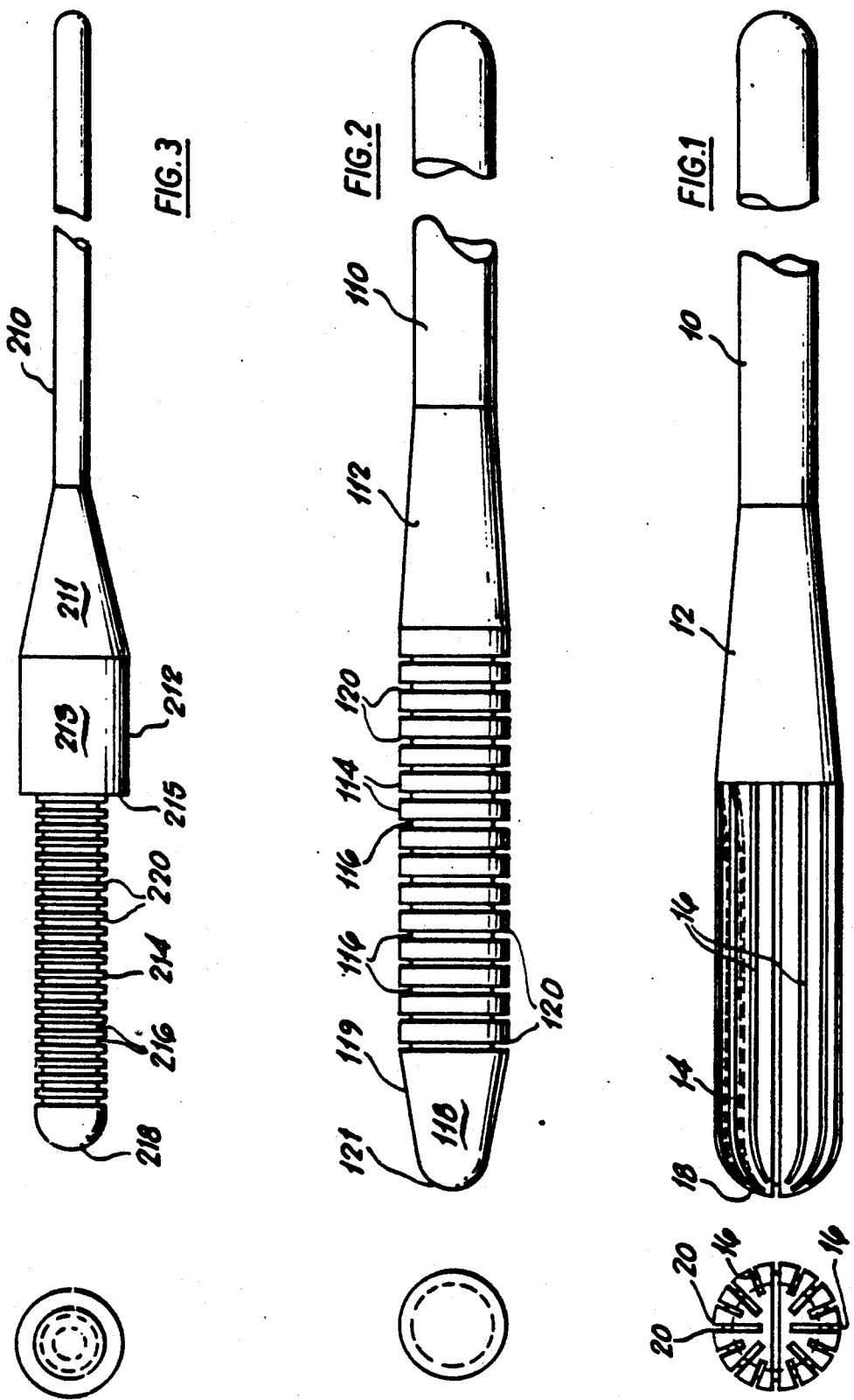

DIAGNOSTIC METHODS

REFERENCE TO RELATED APPLICATIONS

This application is a continuation-in-part of U.S. Ser. No. 913,944 filed Oct. 1, 1986, now abandoned.

BACKGROUND OF THE INVENTION

This invention is concerned with improvements in or relating to the diagnosis of disease particularly, but not exclusively infectious diseases caused by intracellular micro-organisms; as well as being practised on humans in appropriate cases these methods may be practised on animals.

For example, conjunctivitis and keratitis are common eye diseases and may be for example viral, bacterial or chlamydial in causation. The serious eye disease Trachoma is a chlamydial kerato-conjunctivitis. The viruses are commonly adenoviruses or herpes simplex virus.

In the diagnosis of these diseases it is important to have a rapid and reliable method of distinguishing between the chlamydial, adenoviruses and herpes simplex virus infections.

Among the in vitro diagnostic methods available are the direct demonstration method and the culture method. In the direct demonstration method, for example, intact conjunctival cells are smeared onto a slide and assayed by for example immunofluorescent staining techniques. In the culture method, for example, the cell structure in a conjunctival tissue sample is first broken down and then the sample is inoculated onto an appropriate cell culture in order to allow infecting microorganisms multiply; the culture may be treated with ionizing radiation or chemically treated so that any infecting microorganism grows at the expense of retarded cell growth. The incubated sample is then assayed for the presence of micro-organism for example by immunofluorescent staining.

It will be appreciated that both direct demonstration and culture methods require collection of a conjunctival tissue sample directly from the eye. Typically for the direct demonstration method the conjunctival sample is obtained by scraping with a sharp instrument or spatula. In the culture method the sample is obtained by the use of a cotton wool swab, and this also can sometimes be used for the direct demonstration method. In any event these procedures are uncomfortable for the patient and sometimes may not be particularly efficient.

It is an object of the invention to provide an improved probe adapted to collect a conjunctival tissue sample from the eye for assay by for example the culture or direct demonstration method.

The direct demonstration and culture methods are also applicable to cervical or urethral tissue samples. Again cotton wool swabs have been used for obtaining such genital samples, for example mounted on a flexible wire, and these devices are expensive, and again rather inefficient.

The invention provides a probe adapted to collect a mucous tissue sample in vivo comprising (a) a handle portion; (b) a body portion; (c) means for collecting tissue comprising a plurality of slots provided in the body portion, the slots having outer edge portions; and (d) means for scraping tissue into the slots, said tissue scraping means being provided by the outer edge portions of the slots. The width of each slot between its outer edge portion is for example 0.25-0.75 mm.

The probe may be of integral construction or alternatively the body portion could be provided as an item separate from the handle portion with a releasable connection between them so that a single handle portion could be used with a plurality of successive disposable body portions.

SUMMARY OF THE INVENTION

The invention also provides in a probe according to the invention (a) a body portion; (b) means for collecting tissue comprising a plurality of slots provided in the body portion, the slots having outer edge portions; and (c) means for scraping tissue into the slots, said tissue scraping means being provided by the outer edge portions of the slots.

The invention also provides a method of collecting tissue samples in vivo wherein a probe according to the invention is moved along the tissue and the outer edge of the slots scrape the tissue into the slots.

In the culture method, the tissue sample is generally placed in a transport medium, which is inoculated directly onto the cell culture or immediately frozen for storage until the laboratory is ready to test it. However, previously in the direct demonstration method, the sample has been directly smeared onto a slide which can be inconvenient with a sample obtained either by swabbing or by using a probe emodying the present invention.

It is another object of the invention to provide an improved direct demonstration assay method in which a transport medium is used. The transport medium can be used, e.g. for conjunctival, urethral or cervical samples.

The invention also provides a method of diagnosing disease comprising the steps of:

(a) collecting in vivo a tissue sample comprising intact cells;

(b) introducing the tissue sample with the cells intact into an aqueous transport medium comprising:

|  | gms/liter |
| --- | --- |
| sucrose | 130–140 |
| $K_2HPO_4$ | 3.5–4.5 |
| $KH_2PO_4$ | 2–3 |
| pH: 7.1–7.3 | |

(c) smearing the sample from the transport medium, with the cells still intact, onto a slide;

(d) assaying the smear for the disease.

There is further provided a diagnosis kit comprising a probe and a transport medium according to the invention.

The assay step may include, for example, immunofluorescent staining, and may also include for example multiple staining of the smears simultaneously with a plurality of different conjugated antibodies or anti-sera.

Immunofluorescent staining techniques include direct and indirect (sandwich) methods. In the direct method an antibody for the antigen to be detected is conjugated with a fluorescent dye and the conjugated antibody is reacted directly with antigens present in a smear; the antigens are detected as enhanced bright fluorescent areas retained on the smear, unreacted conjugated antibody having been washed off the smear. In the indirect method the antigen to be detected is first reacted with a specific serum containing the relevant antibodies and any such reacted serum will be retained on the smear after washing; the smear is then treated with the appropriate anti-serum conjugated with the fluorescent dye, again followed by washing away of unwanted material. The indirect method is more commonly used in clinical laboratories, but both direct and indirect methods are applicable in the present invention.

In either case specific monoclonal or polyclonal antibodies may be used.

The above and other aspects of the present invention will become more clear from the following description, to be read with reference to the accompanying drawings, of embodiments of the invention. This description, which is illustrative of apparatus, method and kit aspects of the invention, is given by way of example only, and not by way of limitation of the invention.

BRIEF DESCRIPTION OF THE DRAWINGS

Tissue Collection Probes

In the accompanying drawings:

FIG. 1 illustrates an ocular probe embodying the invention;

FIG. 2 illustrates a urethral probe; and

FIG. 3 illustrates a cervical probe.

DESCRIPTION OF SPECIFIC EMBODIMENTS

The ocular probe (FIG. 1) embodying the invention is adapted to collect a mucous tissue sample in vivo from the conjunctiva of the patient. The probe is of integral construction and comprises a cylindrical handle portion 10 for convenient manipulation by the practitioner, and a cylindrical body portion 14 comprising a plurality of axially extending evenly spaced radial slots 16. The body portion 14 is greater in diameter than the handle portion and a frusto-conical intermediate portion 12 extends between the handle portion 10 and the body portion 14.

The body portion 14 comprises a hemispherical nose 18 for comfortable insertion under local anaesthesia behind the patient's eyelids. For manufacturing convenience the slots 16 alternate in radial depth. The slots 16 are rectangular in radial view having sharp outer edges 20. The width of each slot 16 i.e. the distance between its sharp outer edges 20 is for example 0.25-0.5 mm. The diameter of the body portion 14 is for example 3-5 mm. e.g. 4.75 mm. It is preferred to have as many slots as manufacturing procedures will permit for example at least 12, more preferably at least 15; 16 slots are shown in the drawing.

Tha material is of rigid construction and is, for example, stainless steel, in which case the probe can be sterilized for re-use. Alternatively, the probe is disposable, being made from a rigid plastic material, e.g., moulded polystyrene. Rigid material is utilized to form the probes of this invention in order to avoid bending of the probe during use since bending during insertion of the probe could lead to sudden probe movement and result in tissue damage.

In use, the probe is inserted beneath the patient's eyelid and moved along the conjunctival surfaces in a direction transverse to the axis of the probe so that the sharp edges 20 of the slots 16 exert in gentle scraping action. A tissue sample then collects in the slots 16 and can be readily removed therefrom by immersion in transport medium with light stirring or other gentle agitation.

The urethral probe (FIG. 2) embodying the invention is similar in some respects to the ocular probe and is described in so far as it differs therefrom: it is adapted to collect a tissue sample in vivo from the male or female urethra, and comprises a handle portion 110, intermediate portion 112 and body portion 114.

The body portion 114 comprises a plurality of annular slots 116 again with sharp edges 120, and a nose 118 for comfortable insertion into the patients urethra. The nose 118 comprises a frusto-conical portion 119 converging into a hemispherical portion 121. The width of each slot 116 is again for example 0.25-0.5 mm. The diameter of the body portion 114 is for example 3-5 mm e.g. 4 mm. Again it is preferred to have as many slots as possible for example at least 12 more preferably at least 15; 15 slots are shown in the drawing. The axial length of the slotted region between the intermediate portion 112 and the nose 118 is for example at least 10 mm. in order to obtain a representative sample; preferably at least 14 mm. e.g. 14.25 mm.

The cervical probe (FIG. 3) embodying the invention is similar in some respects to the urethral probe and it is described in so far as it differs therefrom: it is adapted to collect a tissue sample in vivo from the cervix of a patient and comprises a handle portion 210, intermediate portion 212 and body portion 214. In this case the intermediate portion 212 is initially frusto-conical at 211 and then becomes cylindrical at 213 to provide an annular shoulder 215 to prevent entry of the probe into the uterus.

The body portion 214 again comprises a plurality of annular slots 216 with sharp edges 220; and a hemispherical nose 218. The width of each slot 216 is for example 0.5-0.75 mm. The diameter of the body portion 214 is for example 5-8.5 mm. e.g. 8 mm. The number of slots is for example at least 15, more preferably at least 20; 21 slots are shown in the drawing. The axial length of the slotted region between the shoulder 215 and the nose 218 is for example 10 mm. The overall length of the body portion from the shoulder 215 to the tip of the nose 218 is at most 20 mm. In using the urethral and cervical probes local anaesthesia is not employed.

EXAMPLE I

Diagnosis Kit comprising Probe and Transport Medium (a) Probe

As described hereinbefore with reference to the drawings.

(b) Transport Medium for Direct Demonstration Method

|  | gms/liter distilled water |
|---|---|
| sucrose | 130-140 e.g. about 137 |
| $K_2HPO_4$ | 3.5-4.5 e.g. about 4 |
| $KH_2PO_4$ | 2-3 e.g. about 2 |

The phosphates provide buffering to a pH just alkaline of e.g. 7.1-7.3.

Preferably the transport medium also comprises: up to 5% by volume (e.g. about 3%) foetal bovine serum, antibiotics e.g. streptomycin, vancomycin, or mixtures thereof and, especially in the case of genital samples, an anti-fungal agent e.g. nystatin.

The quantities of streptomycin, vancomycin and nystantin used are as follows:

| | |
|---|---|
| streptomycin | 100–200 µg/ml |
| vancomycin | 200–400 µg/ml |
| nystatin | 50–100 units/ml. |

The lower ends of these ranges are more appropriate for conjunctival samples and the upper ends more appropriate for genital samples.

The transport medium is hypertonic with respect to the cells to be sampled so that the cells are maintained morphologically intact.

The tissue samples can be kept at room temperature in this medium from up to one to ten days without incubation or other deterioration taking place. It is not necessary or desirable to freeze the samples in the medium.

The diagnosis kit may also include immunofluorescent staining materials.

EXAMPLE I

Immunofluorescent Staining Technique for Detection of Adenovirus, Herpes Simplex virus and Chlamydia by Direct Demonstration A conjunctival sample obtained by swabbing or using the probe of FIG. 1 is suspended in the transport medium of Example I. The transport medium containing the sample is split into two aliquots. The suspended cells in each aliquot are gently sedimented by centrifugation using a cytocentrifuge or by gravity to provide a smear comprising a monolayer of intact cells directly onto a glass slide. Each slide is then washed in pH 7.2 phosphate buffer followed by rinsing in distilled water, and air drying; and the monolayer is fixed by dipping in acetone or methyl alcohol and dried again. One slide is double-stained for detection of adenovirus and herpes simplex virus and the other is separately stained for detection of chlamydia.

EXAMPLE IIa

Double Staining for Detection of Adenovirus and Herpes Simplex

For adenovirus detection a specific serum is used which is for example a commercially available horse anti-adeno type 5 hexons serum (Burroughs Wellcome) and the conjugated anti-serum a commercially available sheep anti-horse fluorescein isothiocyanate (Nordic Laboratories) which yields a bright green stain coloration.

For herpes simplex virus detection the specific serum used is a rabbit anti-herpes simplex serum prepared in my own laboratory by known procedures, and the conjugated anti-serum a commercially available goat anti-rabbit tetramethyl rhodamine isothiocyanate which yields a bright red stain coloration.

The two specific sera are mixed together in a saline solution buffered with phosphate at pH 7.2. A drop of the mixed sera is overlaid on the smear on the slide obtained as described in Example II; and the slide is then incubated at a temperature of about 37° C. for a period of 20–30 minutes at 100% relative humidity to allow the antobodies to attach themselves to any antigens present. The smear is then washed in pH 7.2 phosphate buffer for about 15 minutes and air dried.

The two anti-sera are mixed together in a saline solution buffered with phosphate at pH 7.2. A drop of mixed anti-sera is overlaid on the smear on the slide; and the slide incubated at a temperature of about 37° C. for a period of 20–30 minutes at 100% relative humidity to allow the anti-sera to attach to any specific serum retained on the smear by the antigen-antibody reaction. The smear is again washed in pH 7.2 phosphate buffer for about 15 minutes and air dried.

After drying the slide is dipped in glycerol buffered to pH 7.2 and containing 1, 4 diazobicyclo (2,2,2) octane as an anti-fading agent; a glass cover plate is then placed over the smear, the glycerol providing adhesion between the slide and the cover plate.

The slide is then microscopically viewed separately through red and green optical filters. Bright areas seen through the green filter are positive for adenovirus and bright areas seen through the red filter are positive for herpes simplex virus.

No additional counterstains are necessary to enhance the background for viewing of the smears since the fluorescein isothiocynate and tetramethyl rhodamine isothiocyanate effectively provide counterstaining for each other.

EXAMPLE IIb

Single Staining for Detection of Chlamydia

The specific serum used for example is rabbit anti-chlamydia prepared in my own laboratory and the conjugated anti-serum is commercially available swine anti-rabbit fluorescein isothiocyanate (Nordic Laboratories).

The staining procedure is generally similar to that described in Example IIa except that in this case a tetramethyl rhodamine isothiocyanate counterstain is used to provide a suitable optical background effect.

EXAMPLE III

Staining Technique for Culture Method

Essentially similar staining techniques are used for smears obtained by the culture method except that Giemsa staining may be used as an alternative to immunofluorescent staining for chlamydia detection in smears obtained by the culture method.

EXAMPLE IV

Clinical Tests (a) Transport Medium

| | gms/liter distilled water |
|---|---|
| sucrose | 136.92 |
| $K_2HPO_4$ | 4.176 |
| $KH_2PO_4$ | 2.176 |

The pH was adjusted to 7.1 with HCl.

The solution was then autoclaved at 10 psi for 15 minutes to sterilise it followed by addition of foetal bovine serum to 3% by volume, and the following to the concentrations indicated:

| | |
|---|---|
| streptomycin | 100 µg/ml |
| vancomycin | 200 µg/ml |
| nystatin | 50 units/ml |

The transport medium was dispensed into screw top vials in 0.5 ml aliquots.

(b) Collection of Samples

Samples were taken from the upper and lower lid conjunctiva of patients presenting a mild, moderate or acute conjunctivitis at the Casualty Department, Moorfields Eye Hospital London, England, using cotton wool swabs. The swabs were placed in the vials of transport medium at room temperature, and immediately prior to cytocentrifuging each vial containing the swab in the transport medium was thoroughly agitated by hand to suspend as many cells as possible in the medium while maintaining them intact. The resultant cell suspensions with the swabs removed were transferred to the cytobuckets of a Shandon Cytospin (Shandon Southern Products Limited) and cytocentrifuged directly onto slides at 1700 r.p.m. for 10 minutes. The slides were washed and rinsed; and air dried for ten minutes and the resultant monolayer smears fixed in absolute acetone for ten minutes.

The smears were then assayed for adenovirus alone using a single staining version of the method described in Example IIa with tetramethyl rhodamine isothiocyanate as a counterstain.

The slides were examined using a Zeiss standard 18UV microscope with a filter set 10. The monolayers were scanned at a magnification of X160; any positive indications of infected cells were checked at X400. Specimens were considered positive when at least one intact brightly apple green fluorescent cell could be seen viewed through a specific fluorescein isothiocyanate filter: this showed dull green when seen through a fluorescein isothiocyanate/tetramethyl rhodamine isothiocyanate filter.

The duration of the tests in the laboratory was only 45-90 minutes. 1053 patients were tested and 118 found to be positive for adenovirus.

COMPARATIVE EXAMPLE V

Paired samples from the same 1053 patients were placed in a known transport medium (2SP) for the culture method and immediately frozen in liquid nitrogen. The samples were then thawed, shaken with glass beads to break down the cell structure, centrifuged onto a smear disc and incubated for 48 hours at 35° C. in a culture medium to grow any adenovirus present in the smear: the culture medium comprised a commercially available minimum essential medium (Flow Laboratories Limited, Irvine, Scotland) with the addition of glucose, vitamins and antibiotics. The culture medium was then removed, the smear fixed with methanol, mounted on a slide and tested for adenovirus using the same staining method as in Example IV.

The duration of the laboratory testing was 2-21 days. Of the 1053 patients tested, 110 were found to be positive for adenovirus. Of these 79 had also given positive indications in Example IV.

EXAMPLE VI

Correlation of Positivity between Example IV and Comparative Example V

| | | |
|---|---|---|
| No. of paired samples tested | | 1053 |
| No. of samples positive from Example IV and Comparative Example V | 79 | 53% |
| No. of samples positive from Example IV only | 39 | 26% |
| No. of samples positive from Comparative Example V only | 31 | 21% |
| | 149 | 100% |

I claim:

1. A probe adapted to collect a mucous tissue sample in vivo consisting of (a) a handle portion; (b) a rigid body portion; (c) means for collecting tissue comprising a plurality of continuous and nonintersecting slots provided in the body portion; the slots having outer edge portions to effect tissue scraping wherein the width of each slot between its outer edge portions is selected from the group consisting of (1) 0.25 to 0.5 mm and (2) 0.5 to 0.75 mm and said rigid body portion in the region of the slots having a diameter selected from the group consisting of (1) between 3 and 5 mm and (2) between 5 and 8.5 mm and wherein the width of the body portion between said slots in greater than the width of said slots.

2. A probe according to claim 1 wherein the outer edge portions of the slots are sharp.

3. A probe according to claim 1, wherein the width of each slot between its outer edge portions is 0.25-0.5 mm.

4. A probe according to claim 1, wherein said slots comprise at least twelve evenly spaced slots.

5. A probe according to claim 1 of integral metallic construction.

6. A probe according to claim 1 of integral plastic construction.

7. A probe according to claim 1, adapted to collect a tissue sample from the conjunctiva, wherein the body portion is cylindrical in the region of the slots, the slots are radial and extend axially of the probe.

8. A probe according to claim 7, wherein said slots comprise at least fifteen evenly spaced slots.

9. A probe according to claim 7 wherein the diameter of the body portion in the region of the slots is 3-5 nm.

10. A probe according to claim 1 adapted to collect a tissue sample from the conjunctiva or urethra wherein the width of each slot between its outer edge portions is 0.25-0.5 mm.

11. A probe according to claim 1, adapted to collect a tissue sample from the cervix, wherein the width of each slot between its outer edge portions is 0.5-0.75 mm.

12. A probe according to claim 1 adapted to collect a tissue sample from the urethra or cervix wherein the body portion is cylindrical in the region of the slots and the slots are annular.

13. A urethral probe according to claim 12 wherein said slots comprise at least fifteen evenly spaced slots.

14. A urethral probe according to claim 10, wherein the diameter of the body portion in the region of the slots is 3-5 mm.

15. A urethral probe according to claim 12, wherein the axial length of the slotted region is at least 10 mm.

16. A urethral probe according to claim 12, wherein the axial length of the slotted region is at least 14 mm.

17. A cervical probe according to claim 12 wherein said slots comprise at least twenty evenly spaced slots.

18. A cervical probe according to claim 12 wherein the diameter of the body portion in the region of the slots is 5-8.5 mm.

19. A cervical probe according to claim 12 wherein the axial length of the slotted region is 10-20 mm.

20. A cervical probe according to claim 12 wherein the body portion defines annular shoulder means for preventing entry of the probe into the uterus.

21. A cervical probe according to claim 20 wherein the body portion terminates in nose means for comfortable insertion into the cervix and the length of the body portion from the annular shoulder to the tip of the nose is at most 20 mm.

* * * * *